United States Patent [19]

Lett et al.

[11] Patent Number: 5,723,638
[45] Date of Patent: Mar. 3, 1998

[54] PROCESS FOR 20-OXO-17α,21-DIOL STEROIDS

[75] Inventors: Robert Lett, Paris; Oleg Melnyk, Mons-en-Baroeul, both of France

[73] Assignee: Roussel Uclaf, France

[21] Appl. No.: 495,048

[22] Filed: Jun. 26, 1995

[30] Foreign Application Priority Data

Jul. 1, 1994 [FR] France ................... 94 08140

[51] Int. Cl.[6] .................. C07J 75/00; C07J 5/00
[52] U.S. Cl. .................. 552/558; 552/517; 552/518; 552/520; 552/577; 552/593; 552/595; 540/30; 540/34; 540/100; 540/101
[58] Field of Search .................... 552/517, 518, 552/520, 558, 577, 595, 593; 540/30, 34, 100, 101

[56] References Cited

FOREIGN PATENT DOCUMENTS 0531212  3/1993  France .

OTHER PUBLICATIONS

An International Journal of Reviews & Communications in Heterocycli Chemistry Article. vol., 17 1982, Daniel Flynn, et al, pp. 83–86.

*Primary Examiner*—Kimberly J. Prior
*Attorney, Agent, or Firm*—Bierman, Muserlian and Lucas, LLP

[57] ABSTRACT

The invention is drawn to a process for the preparation of a steroid of the formula

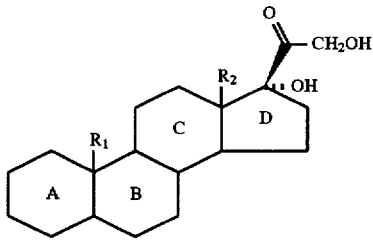

wherein $R_1$ is hydrogen or alkyl of 1 to 4 carbon atoms, $R_2$ is alkyl of 1 to 4 carbon atoms and the o A, B, C, and D ring system has at least one double bond and is optionally substituted by at least one optionally protected hydroxy, optionally protected keto, halogen, alkyl and alkoxy of 1 to 4 carbon atoms, and alkenyl and alkynyl of 2 to 4 carbon atoms by reacting the corresponding 17-ketosteroid with a compound of the formula

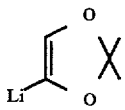

and then by reacting the resulting compound with an aryl sulfenyl halide. The intermediate produced then undergoes rearrangement followed by epimerization with a strong base to obtain a mixture of the corresponding sulfoxide diastereoisomers which is reacted with a thiophilic compound. The intermediate produced undergoes acid hydrolysis to provide the compound of formula I.

12 Claims, No Drawings

PROCESS FOR 20-OXO-17α,21-DIOL STEROIDS

OBJECTS OF THE INVENTION

It is an object of the invention to provide a novel process for the preparation of steroids of formula I.

It is another object of the invention to provide novel intermediates prepared in the process.

These and other objects and advantages of the invention will become obvious from the following detailed description.

THE INVENTION

The novel process of the invention for the preparation of a steroid of the formula

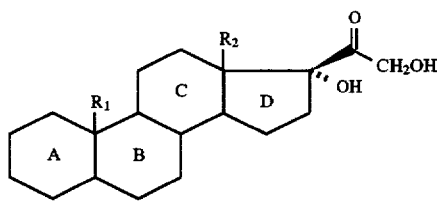

wherein $R_1$ is hydrogen or alkyl of 1 to 4 carbon atoms, $R_2$ is alkyl of 1 to 4 carbon atoms and the A, B, C and D ring system has at least one double bond and the A, B, C and D ring optionally substituted by at least one member of the group consisting of optionally protected hydroxy, optionally protected keto, halogen, alkyl and alkoxy of 1 to 4 carbon atoms and alkenyl and alkynyl of 2 to 4 carbon atoms comprises reacting a compound of the formula

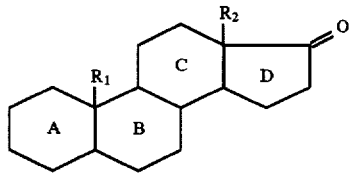

wherein $R_1$, $R_2$, A, B, C and D are as defined above with a reagent of the formula

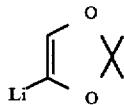                                    R to obtain a compound of the formula

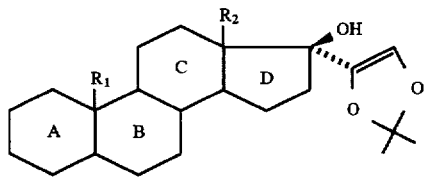                                   III wherein $R_1$, $R_2$, A, B, C and D are as defined above, reacting the latter with an aryl sulfenyl halide of the formula Ar-S-Hal                                              S wherein Ar is an optionally substituted phenyl and Hal is halogen in the presence of a base to obtain intermediately a compound of the formula

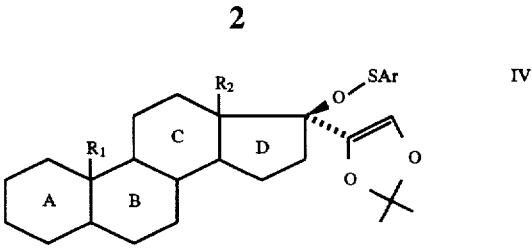                                   IV wherein Ar is defined as above which is rearranged optionally in the presence of a base into the sulfoxide of the formula

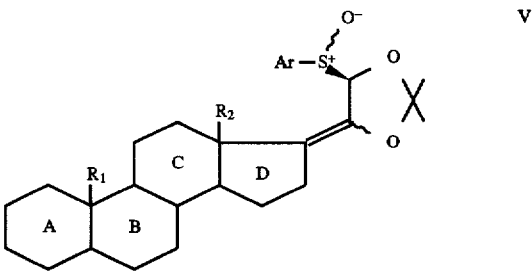                                   V which is in the form of a mixture of diasteroisomers of E+Z configuration at the level of the 17(20) double bond, reacting the latter with an epimerization agent to obtain the sulfoxides of the formula

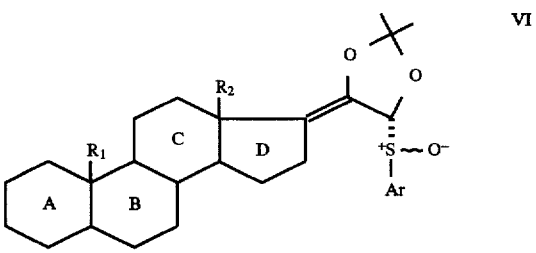                                   VI which are in form of a mixture of diastereoisomers of (Z) configuration at the level of the 17(20) double bond and which are in equilibrium with the sulfenate of the formula

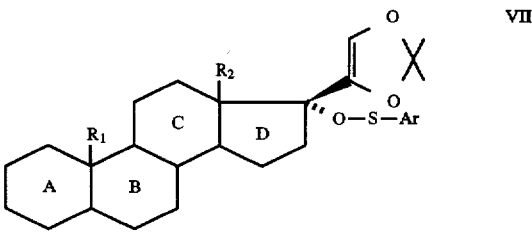                                   VII cleaving the latter with a thiophilic compound to obtain a compound of the formula

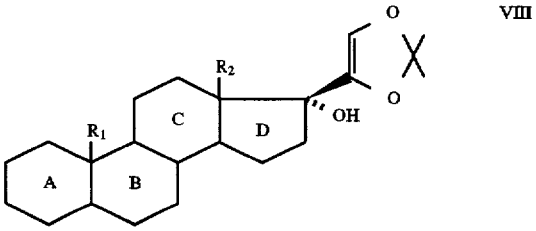                                  VIII and reacting the latter with an acid hydrolysis agent to obtain the compound of formula I.

When $R_1$ is alkyl, it is preferably methyl or ethyl. $R_2$ is preferably methyl or ethyl.

When nuclei A, B, C and D carry one or more double bonds, they are preferably double bonds in position 1(2), 3(4), 4(5) or 9(11) or a system of double bonds conjugated in positions 3(4) and 5(6) or in positions 4(5) and 6(7) or in positions 1(2) and 4(5) or an aromatic system with three double bonds 1,3,5(10) or a system of three double bonds 1(2), 4(5), 6(7).

When rings, A, B, C and D are substituted by one or more hydroxyls, it is preferably a hydroxyl in position 3, in position 9 or in position 11. When the hydroxyls are protected, it can be any type of protection known to a one skilled in the art and preferably a protection in the form of organic acid esters, such as acetic acid, propionic acid, formic acid or benzoic acid, or lower alkyl ethers, such as methyl or ethyl, of an alkoxy, alkoxyalkyl, such as methoxyethoxymethyl, of an aralkyl, such as benzyl or phenethyl, of an aryl such as optionally substituted phenyl, silylated ethers such as trialkylsilyl such as trimethyl or dimethyl-tert-butylsilyl, triarylsilyl such as triphenylsilyl or diarylalkylsilyl such as diphenyl tert-butylsilyl, or also an ether of tetrahydropyranyl.

Widen rings A, B, C and D are substituted by one or more ketones, it is preferably a ketone in position 3 or in position 11. When the ketone in position 3 is protected, it is preferably a protection in the form of a ketal or a thioketal whether cyclic or not, or an enol ether or ester or also an oxime, hydrazone or semi-carbazone and when the ketone function in position 11 is protected, it is preferably in the form of an enol ether or ester. Examples of ketone protections in the form of esters and ethers are provided above.

When rings A, B, C and D are substituted by one or more halogens, it is preferably fluorine, chlorine or bromine in position 6 or 9α. When rings A, B, C and D are substituted by one or more alkyls, it is preferably methyl or ethyl in position 2, 6, 7, in position 16α or in 16β. When rings A, B, C and D are substituted by one or more alkoxyls, it is preferably methoxy or ethoxy in position 3 or 11β. When rings A, B, C and D are substituted by one or more alkenyls, it is preferably vinyl or allyl in position 6 or 11β. When rings A, B, C and D are substituted by one or more alkynyls, it is preferably ethynyl in position 6 or 11β.

In a preferred mode of the process the compound of formula II correspond to the formula

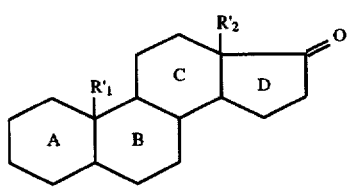

wherein $R'_1$ is hydrogen or methyl, $R'_2$ is methyl or ethyl and nuclei A, B, C and D carry one or more double bonds in position 1(2), 3(4), 4(5) or 9(11) or 3(4) and 5(6) or 4(5) and 6(7) or 1(2) and 4(5) or 1,3,5(10) or 1(2), 4(5) and 6(7) and are optionally substituted by one or more hydroxyls in position 3, 9 and/or 11, by one or two ketones in position 3 and/or 11, the ketone in position 3 being protected, by one or two fluorine, chlorine or bromine in position 6 and/or 9α, by one or more methyl or ethyl in position 2, 6, 7 and/or 16α or 16β, by one or two methoxy or ethoxy in position 3 and/or 11β, by a vinyl or allyl in position 11β or by ethynyl in position 11β.

A more preferred process of the invention comprises using a compound of formula II corresponding to the formula

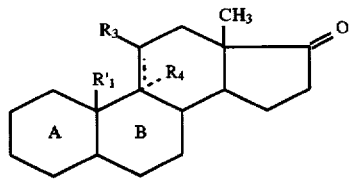

wherein $R'_1$ is defined as above, the dotted line in position 9(11) is an optional second bond, $R_3$ is hydrogen, oxo or hydroxy optionally protected in the form of an ether or ester, $R_4$ is hydrogen, hydroxy or fluorine, rings A and B represent one of the following remainders:

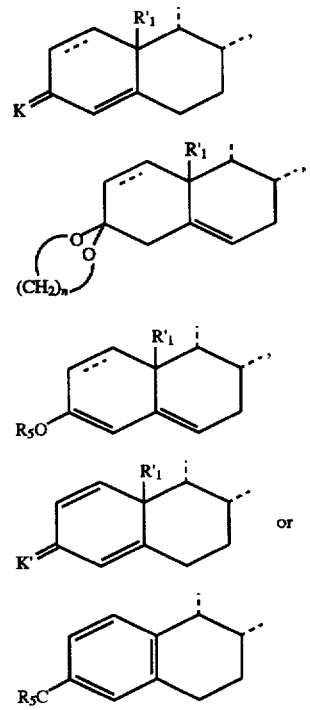

in which the dotted line in the ring A is an optional second bond, K is an oxo protected in the form:

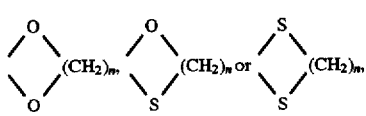

n being 2 or 3, $R_5$ is an ether or ester remainder, K' is an oxo protected in the form of an oxime, hydrazone or semi-carbazone. The values of $R_5$ are particularly the preferred values of the ether and ester remainders mentioned above.

The second bond in position 9(11) is optionally only present when the substitutions in positions 9 and 11 allow it, and the products of formulae II, II' and II" are known products or products which can be prepared by processes known to a man skilled in the art.

The reagent R is preferably prepared in situ and the condensation on the compound of formula II is preferably carried out in an ether such as tetrahydrofuran or dioxane at a temperature of −70° to −80° C.

The sulfenylation agent of formula S is preferably phenyl, 3-nitrophenyl or 3,4-dinitrophenyl sulfenyl chloride or bromide. The sulfenylation reaction is carried out in the presence of a base which is preferably a tertiary amine such as triethylamine, pyridine, 4-dimethylamino-pyridine, N-methylimidazole or diazabicyclo-octane, or also a mixture of these bases. The operation is preferably carried out under the same solvent conditions as above and at a temperature preferably between −80° and −40° C.

The rearrangement into the sulfoxide of formula V is carried out thermally by allowing the temperature to rise to ambient temperature. An excess of base which preferably is triethylamine, pyridine or diazabicyclo-octane is preferably added to the reaction medium, if the operation is carried out in the presence of 4-dimethylamino-pyridine or N-methyl imidazole. If desired, the mixture of diastereoisomers obtained can be separated, for example by chromatography.

The epimerization agent which is reacted on the mixture of sulfoxides of formula V is a strong base, for example an ammonium hydroxide such as tetrabutyl or N-benzyltrimethyl ammonium hydroxide or an alkali metal hydroxide, particularly sodium potassium or lithium hydroxide, or also another nitrogen base. An alkali metal carbonate or bicarbonate can also be used. The operation is carried out in an aqueous or alcoholic polar medium, for example aqueous methanol and preferably in the presence of a cosolvent which can be particularly dimethylsulfoxide or dimethylformamide.

Cleavage of the sulfenate of formula VII is carried out by the action of a thiophilic agent which is preferably one of the strong bases mentioned above for the epimerization, which therefore displaces the equilibrium in said epimerization. However, any standard thiophilic agent can be used such as trialkyl phosphites such as trimethyl- or triethylphosphite, a secondary amine such as diethylamine or piperidine or also a thiolate such as ArS⁻, for example sodium thiophenolate or thiophenol in the presence of a tertiary amine.

The hydrolysis of the compound of formula VIII is carried out by the action of a mineral or organic acid, for example hydrochloric acid, hydrobromic acid, sulfonic acid, formic acid, acetic or p-toluene sulfonic acid, hydrochloric acid being preferred. It can be carried out in a homogeneous medium, but advantageously the operation is carried out in a two phase medium, in the presence of water and a halogenated organic cosolvent such as methylene chloride, an ester such as ethyl acetate, an ether such as ethyl ether or an aromatic solvent such as benzene or toluene.

Preferably the process is characterized in that the operation is carried out without intermediate isolation of the compounds of formulae III to VII. The operating conditions are those which have been described above. A diagram of the process in its totality is shown hereafter.

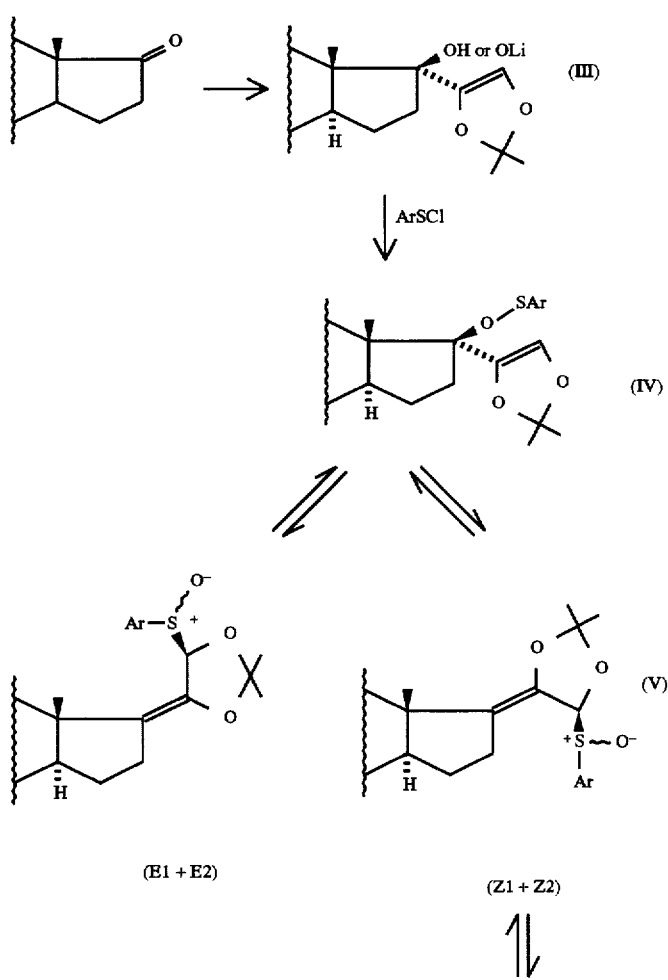

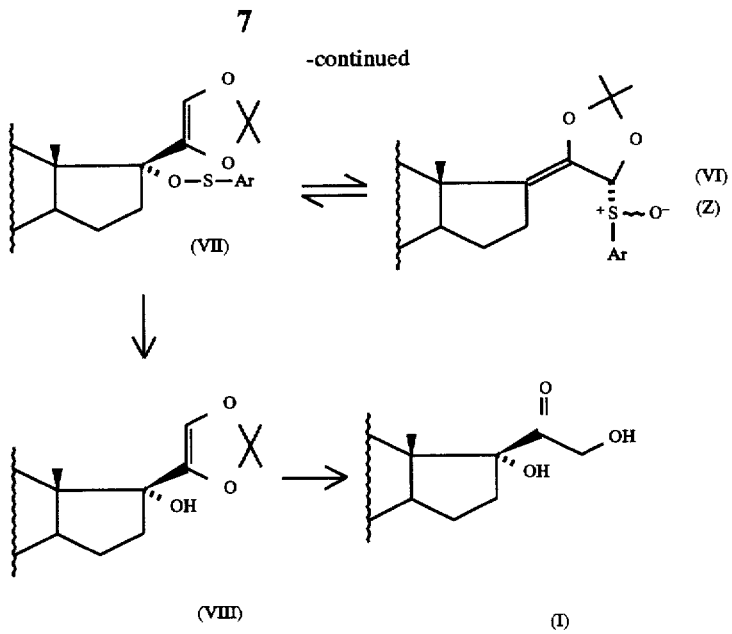

The corticosteroids of formula I are generally known, whether they are compounds in which the optional reactive functions are protected or not, or can be used to prepare known products, by processes known themselves either of simple deprotection of the protected functions, or more elaborate chemical conversions.

The hydrolysis of a compound of type III obtained by the action of reagent R on methylestrone has already been attempted by Mitscher et al., Heterocycles, 1982, Vol. 18, pp. 83–86, with the object of obtaining the corresponding 17-dihydroxyketone of inverse configuration to the compounds of formula I of the invention. This hydrolysis was not able to be realized, the authors having only obtained a mixture of enol-aldehydes E & Z of the formula:

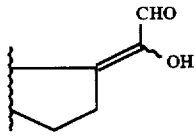

resulting from the elimination of the 17β-OH.

At the level of the final hydrolysis of the compound of formula VIII, the invention has therefore solved this problem.

Other examples of access to structures of cortisonic type via compounds derived from 1,4-dioxene or 1,2-dimethoxyethylene (German Patents No. 2,521,231, No. 2,603,266, No. 2,655,104 and U.S. Pat. No. 4,089,852, Tet. Letters, 1985, Vol. 26, pp. 4925–4928) have been described. However, these do not use rearrangements such as those described in the present invention. Rearrangements of allylic sulfenates into allylic sulfoxides have been described by syntheses of corticosteroids, particularly in German Patent No. 2,256,866 or the references J. Org. Chem., 1976, Vol. 41, pp. 2312–2314 or 1979, Vol. 44, pp. 1582–1584. However, they indicate intermediates of a completely different nature.

The compounds of formulae IV, V, VI, VII and VIII, as well as the compounds of formula III with the exception of the methylestrone derivative, are new and another object of the invention are these compounds as new industrial products and particularly intermediates in the implementation of the process of the invention.

In the following examples, there are described several preferred embodiments to illustrate the invention. However, it should be understood that the invention is not intended to be limited to the specific embodiments.

EXAMPLE 1

3-methoxy-19-nor-Δ1,3,5(10)-pregnatrien-17α,21-diol-20-one

STAGE A: 20,21-(cyclic 1-methylethylidene acetal) of 3-methoxy-19-nor-Δ1,3,5(10),20-pregnatetraene-17α,20,21-triol 2.43 ml (3.89 mmoles) of 1.6M n-butyllithium in n-hexane were added over 5 minutes to 478 μl (4.05 mmoles) of vinylene acetonide in solution in 5 ml of anhydrous tetrahydrofuran at −78° C. and under argon. After 15 minutes, the reaction medium was placed in a bath at −30° C. with stirring for 1 hour. A solution of 552 mg (1.94 mmole) of methylestrone in 13 ml of anhydrous tetrahydrofuran were added over 20 minutes. After 1 hour, the mixture was hydrolyzed with 10 ml of a saturated aqueous solution of sodium bicarbonate and was extracted with 3×50 ml of ether. The combined organic phases were washed with 50 ml of a saturated aqueous solution of sodium bicarbonate, then filtered through sodium sulfate. After evaporation of the solvents, the crude product was purified by chromatography on silica ($CH_2Cl_2$ 98/AcOEt 2) to obtain 630 mg (84%) of the expected product.

NMR $^1$H 200 MHz ($C_5D_5N$): 7.10 (d, 1H, $H_1$, $J_{1-2}$=8.5 Hz); 6.68 (dd, 1H, $H_2$, $J_{2-1}$=8.5 Hz, $J_{2-4}$=3 Hz); 6.57 (d, 1H, $H_4$, $J_{4-2}$=3 Hz); 6.35 (s, 1H, $H_{21}$); 6.30 (ws, 1H exch., OH); 3.49 (s, 3H, OMe); 1.39 (s, 3H, C($CH_3$)); 1.36 (s, 3H, C($CH_3$)); 0.98 (s, 3H, $Me_{18}$).

IR ($CHCl_3$): 3575 (free OH) 3490 (ass. OH) 1609-1576-1500 (Ar) 1383 and 1373 (C($CH_3$)$_2$).

STAGE B: cyclic 1-methylethylidene acetal of 3-methoxy-21-(phenylsulfinyl)-19-nor-Δ1,3,5(10),17(20) pregnatetraene-20,21-diol 85.6 mg (0.22 mmole) of the product of Stage A, 4.0 mg (33 μmoles) of 4-dimethylamino-pyridine and 155 μl (1.11 mmole) of triethylamine were solubilized at −40° C. and under argon in 5 ml of anhydrous tetrahydrofuran and 25 μl (0.21 mmole)) of benzenesulfenyl chloride were added over 30 minutes. Another 5 µl (43 µmoles) of benzenesulfenyl chloride were added and stirring was continued for 90 minutes. 250 µl (1.79 mmole) of triethylamine were added and the cooling bath was removed. The medium was hydrolyzed at room temperature with 40 ml of a saturated aqueous solution of sodium bicarbonate and 40 ml of water and then was extracted 3 times with 50 ml of dichloromethane. The combined organic phases were filtered through sodium sulfate after having added 5 drops of pyridine. After evaporation of the solvents, the crude product was purified by chromatography on silica ($CH_2Cl_2$ 95/AcOEt 5/pyridine 0.2) to obtain 82.1 mg (75%) of the expected sulfoxides. After chromatographing on silica (eluant $CH_2Cl_2$ 96/AcOEt 4/pyridine 0.2), 14% of the expected product in the form of isomer Z and 27% of the expected product in the form of isomer E were obtained.

Isomer E: mixture of 2 diastereoisomers (8/2) (21R, sulfur epimers)

NMR $^1$H 200 MHz ($C_5D_5N$): 7.8–7.2 (m, 5H, SPh); 7.11 (d, 1H, $H_1$, $J_{1-2}$=8.5 Hz); 6.73 (dd, 1H, $H_2$, $J_{2-1}$=8.5 Hz, $J_{2-4}$=3 Hz); 6.61 (d, 1H, $H_4$, $J_{4-2}$=3 Hz); 5.76 (s, 0.8 H, $H_{21alpha}$); 5.58 (s, 0.2 H, $H_{21alpha}$); 3.58 (s, 2.4 H, OMe); 3.50 (s, 0.6 H, OMe); 1.63 (s, 2.4 H, C($CH_3$)); 1.22 (s, 0.6 H, C($CH_3$)); 1.18 (s, 2.4 H, C($CH_3$)); 1.15 (s, 0.6 H, 0.6 H, $Me_{18}$); 1.30 (s, 2.4 H, $Me_{18}$).

Isomer Z: mixture of 2 diastereoisomers (8/2) (21S, sulphur epimers)

NMR $^1$H 200 MHz ($C_5D_5N$): 7.8–7.2 (m, 5H, SPh); 7.09 (d, 1H, $H_1$, $J_{1-2}$=8.5 Hz); 6.69 (dd, 1H, $H_2$, $J_{2-1}$=8.5 Hz, $J_{2-4}$=3 Hz); 6.60 (d, 1H, $H_4$, $J_{4-2}$=3 Hz); 5.41 (s, 0.8 H, $H_{21alpha}$); 5.36 (s, 0.2 H, $H_{21alpha}$); 3.49 (s, 3 H, OMe); 1.56 (s, 2.4 H, C($CH_3$)); 1.21 (s, 0.6 H, C($CH_3$)); 1.18 (s, 2.4 H, C($CH_3$)); 1.15 (s, 0.6 H, C($CH_3$)); 0.82 (s, 0.6 H, $Me_{18}$); 0.75 (s, 2.4 H, $Me_{18}$).

STAGE C: 20,21-(cyclic 1-methylethylidene acetal) of 3-methoxy-19-nor-Δ1,3,5(10),20-pregnatetraene-17,20,21-triol 30.4 mg (61.7 µmoles) of the E sulfoxides of Stage B and 0.5 ml (1.1 mmole, 40% in methanol) of triton B (N-benzyl trimethylammonium hydroxide) were stirred for 16 hours at ambiemt temperature in 2 ml of dimethylsulfoxide. The medium was hydrolyzed with 20 ml of a saturated aqueous solution of sodium bicarbonate and were extracted with 100 ml of a $CH_2Cl_2$ 1/AcOEt 1 mixture- The organic phase was washed twice with 25 ml of a saturated aqueous solution of sodium bicarbonate diluted 5 times and was filtered through a short column of sodium sulfate after having added 1 drop of pyridine. After evaporation of the solvents, the crude product was purified by chromatography on silica (toluene 96.2/AcOEt 3.6/pyridine 0.2) to obtain 9.3 mg (39%) of the expected product.

16.2 mg (32.9 µmoles) of the Z sulfoxides of Stage B and 0.25 ml (0.55 mmole, 40% in methanol) of triton B were stirred for 16 hours at ambient temperature in 2 ml of dimethylsulfoxide. Treatment and purification were identical to the preceding operating method to obtain 8.2 mg (65%) of the expected product melting at 121°–122° C. (Kofler)

NMR $^1$H 200 MHz $C_5D_5N$): 7.09 (d, 1H, $H_1$, $J_{1-2}$=8.5 Hz); 6.68 (dd, 1H, $H_2$, $J_{2-1}$=8.5 Hz, $J_{2-4}$=3 Hz); 6.58 (d, 1H, $H_4$, $J_{4-2}$=3 Hz); 6.30 (s, 1 H, $H_{21}$); 6.02 (ws, 1 H exch., OH); 3.50 (s, 3 H, OMe); 1.38 (s, 3 H, C($CH_3$)); 1.28 (s, 3H, C($CH_3$): 0.71 (s, 3 H, $Me_{18}$).

MS (SIMS BNA matrix): m/z=384 ($M^+$), 367 ($MH^+$-$H_{20}$); 326 ($M^+$-$Me_2CO$).

IR ($CHCl_3$): 3586 (OH); 1608-1575-1500 (MeO-Ar); 1383 and 1373 (C($CH_3$)$_2$).

UV (EtOH): 278 (2400); 287 (2300).

STAGE D: 3-methoxy-19-nor-Δ1,3,5 (10)-pregnatrien-17α, 21-diol-20-one 0.33 ml (0.33 mole) of 1N hydrochloric acid saturated with sodium chloride were added to 14.4 mg (37.4 µmoles) of the product of Stage C dissolved in 3.3 ml of dichloromethane at ambient temperature. The medium was vigorously stirred for 15 minutes and then reacted and purified as previously to obtain 5.9 mg (46%) of the expected product melting at 182° C. (Kofler).

NMR $^1$H 200 MHz (CDCl$_3$): 7.20 (d, 1H, $H_1$, $J_{1-2}$=8.5 Hz); 6.72 (dd, 1H, $H_2$, $J_{2-1}$=8.5 Hz, $J_{2-4=3}$ Hz); 6.64 (d, 1H, $H_4$, $J_{4-2}$=3 Hz); 4.71 (dd, 1 H, $H_{21}$, $^2J$=20 Hz, $J_{21-OH}$=5 Hz); 4.35 (dd, 1 H, $H_{21}$,1, $^2J$=20 Hz, $J_{21-OH}$=5 Hz); 3.78 (s, 3 H, OMe); 3.12 (t, 1H exch., $CH_2OH$, $J_{OH-21}$=5 Hz); 2.19 (s, 1H exch., OH); 0.71 (s, 3H, $Me_{18}$).

MS (FD BNA matrix): m/z=344 ($M^+$, 100%).

IR (CHCl$_3$): 3610 (free OH); 3505 (ass. OH); 1700 (C=O); 1575 and 1500 (MeO-Ar).

UV (EtOH): 279 (2100); 287 (2000).

EXAMPLE 2

3-methoxy-19-nor-Δ1,3,5(10)-pregnatrien-17α,21-diol-20-one

STAGE A: 3 -methoxy-20,21-(dimethylmethylenedioxy) -17β-Δ1,3,5(10),20-pregnatetraen-17α-ol 550 µl (0.88 mmole) of 1.6M n-butyllithium in n-hexane were added over 10 minutes to 105.3 µl (0.89 mmole) of vinylene acetonide in solution in 1 ml of anhydrous tetrahydrofuran at −78° C. and under argon. The flask was placed in an acetone bath at −40° C. for 1 hour and 110.2 mg (0.387mmole) of methylestrone dissolved in 4.5 ml of tetrahydrofuran were added over 10 minutes. After 1 hour, 70.8 mg (0.58mmole) of 4-dimethylamino-pyridine dissolved in 1 ml of tetrahydrofuran were added and 200 µl (1.7 mmole) of benzene sulfenyl chloride were added over 2 hours 15 minutes. When the addition was finished, the excess benzene sulfenyl chloride was destroyed with 100 µl (2.48 mmoles) of methanol. 436 mg (3.89 mmoles) of DABCO were added and the cooling bath was removed. The mixture was diluted at ambient temperature with 10 ml of dimethylsulfoxide and heated to 50° C. under a partial vacuum of 30 mm Hg (heating started 30 minutes after having removed the acetone bath). After 45 minutes, 1.5 ml (3.8 mmoles, 40% in water) of triton B were added at ambient temperature and under argon. The medium was stirred for 75 minutes adn cooled to 0° C. to hydrolyze with 100 ml of a saturated aqueous solution of sodium bicarbonate. The aqueous phase was extracted six times With 50 ml of cyclohexane. The combined organic phases were washed with 50 ml of a saturated aqueous solution of sodium bicarbonate and filtered through a short column of sodium sulfate after adding 0.5 ml of pyridine. After evaporating the solvents, the crude product was purified by flash chromatography on silica (toluene 96.4/AcOEt 3.6/pyridine 0.2) to obtain 66.1 mg (44%) of 3-methoxy-20,21-(dimethylmethylenedioxy)-17β-Δ1,3,5(10),20-pregnatetraen-17α-ol.

STAGE B: 3-methoxy-19-nor-Δ1,3,5(10)pregnatrien-17α, 21-diol-20-one

Using the procedure of Stage D of Example 1, the expected product was obtained.

EXAMPLE 3

4-pregnene-17α,21-diol-3,11,20-trione

STAGE A: 3-methoxy-20,21-[(1-methylethylidene)-bis(oxy)]-Δ3,5,20-pregnatrien-17α-ol-11-one 1.20 ml (1.92 mmole) of 1.6M n-butyllithium in hexane were added over 5 minutes to 237 µl (1.98 mmole) of vinylene acetonide dissolved in 5 ml of tetrahydrofuran at −78° C. and under argon. After 15 minutes, the flask was placed in an acetone bath at −40° C. for 1 hour and the medium was then cooled to −78° C. 263.8 mg (0.84 mmole) of 3-methoxy-Δ3,5-androstadiene-11,17-dione dissolved in 5 ml of tetrahydrofuran were added over 15 minutes and after 45 minutes, the medium was hydrolyzed with 30 ml of a saturated aqueous solution of sodium bicarbonate, then extracted twice with 100 ml of ether. The combined organic phases were washed twice with 30 ml of a saturated aqueous solution of sodium bicarbonate, then filtered through a short column of sodium sulfate after having added 5 drops of pyridine. After evaporation of the solvents, the crude product was purified by flash chromatography on silica (toluene 87/AcOEt 13/pyridine 0.2) to produce a solution of the pure expected product to which 102.6 mg (0.84mmole) of 4-dimethylaminopyridine were added before evaporation of the solvents to obtain 350.0 mg of a mixture containing 71% by mass of the expected product i.e. 247.4 mg of pure product.

NMR $^1$H 200 MHz (CDCl$_3$+0.4% of C$_5$D$_5$N): 6.12 (s, 1H, H$_{21}$); 5.19 (m, 1H, H$_6$); 5.09 (d, 1H, H$_4$, J=1 Hz); 3.57 (s, 3H, OMe); 1.56 (s, 3H, C(CH$_3$)); 1.50 (s, 3H, C(CH$_3$)); 1.16 (s, 3H, Me$_{19}$); 1.07 (s, 3H, Me$_{18}$).

STAGE B: 3-methoxy-20,21-[(1-methylethylidene)-bis(oxy)]21-(phenylsulfinyl)-Δ3,5,17(20)-pregnatrien-11-one 92.4 mg (0.22m mole) of the product of Stage A stabilized with 70.2 µl (0.88 mmole) of N-methyl imidazole and 155 µl (1.10 mole) of triethylamine were solubilized in 2.4 ml of anhydrous tetrahydrofuran at −40° C. and under argon. 700 µl (0.54 mole) of 0.78M benzene sulfenyl chloride in tetrahydrofuran were added over 90 minutes. The medium was hydrolyzed at −40° C. with 30 ml of a saturated aqueous solution of sodium bicarbonate and extracted with 100 ml, then 50 ml of ether. The combined organic phases were washed three times with 30 ml of a saturated aqueous solution of sodium bicarbonate, then filtered through a short column of sodium sulfate after having added 0.5 ml of pyridine. After evaporating the solvents, the crude product was purified by flash chromatography on silica (CH$_2$Cl$_2$ 95/AcOEt 5/pyridine 0.2) to produce 20.0 mg (17%) of isomer E and 59.9 mg (51%) of isomer Z.

Isomer E: (21R)

NMR $^1$H 200 MHz (C$_5$D$_5$N): 7.7–7.1 (m, 5H, Ph); 5.72 (s, 1H, H$_{21alpha}$); 5.09 (m, 2H, H$_6$, H$_4$); 3.34 (s, 3H, OMe); 2.91 (d, 1H, H$_{12}$, $^2$J=12 Hz); 2.67 (dd, 1H, H$_x$, J=12 and 5 Hz); 2.48 (d, 1H, H$_{12}$, $^2$J=12 Hz); 1.59 (s, 3H, Me$_{19}$); 1.16 (s, 6H, C(CH$_3$)$_2$); 0.95 (s, 3H, Me$_{18}$).

Z isomers: (21S ', sulfur epimers)

Isomer Z$_1$:

NMR $^1$H 200 MHz (C$_5$D$_5$N): 7.7–7.2 (m, 5H, Ph); 5.44 (s, 1H, H$_{21alpha}$); 5.10 (m, 2H, H$_6$, H$_4$); 3.30 (s, 3H, OMe); 3.06 (d, 1H, H$_{12beta}$, $^2$J=13 Hz); 2.68 (dd, 1H, H$_x$, J=13 and 4 Hz); 2.32 (dl, 1H, H$_{12alpha}$, $^2$J=13 Hz); 1.48 (s, 3H, Me$_{19}$); 1.11 (s, 3H, C(CH$_3$)); 1.09 (s, 3H, C(CH$_3$); 0.75 (s, 3H, Me$_{18}$).

Isomer Z$_2$:

NMR $^1$H 200 MHz (C$_5$D$_5$N): 7.75–7.20 (m, 5H, Ph); 5.33 (s, 1H, H$_{21alpha}$); 5.09 (m, 2H, H$_6$, H$_4$); 3.29 (s, 3H, OMe); 3.07 (d, 1H, H$_{12beta}$, $^2$J=13 Hz); 2.88 (dd, 1H, H$_x$, J=17 and 9 Hz); 2.68 (dd, 1H, H$_x$, J=12.5 and 4 Hz); 2.32 (wd, 1H, H$_{12alpha}$, $^2$J=13 Hz); 1.17 (s, 3H, Me$_{19}$); 1.12 (s, 3H, C(CH$_3$)); 1.06 (s, 3H, C(CH$_3$); 0.82 (s, 3H, Me$_{18}$).

STAGE C: 3-methoxy-20,21-[(1-methyl ethylidene)-bis(oxy)]-Δ3,5,20-pregnatrien-17α-ol-11-one 1st method:

77.3 mg (0.148 mole) of the sulfoxides of Stage B were solubilized at ambient temperature and under argon in 12 ml of dimethylsulfoxide and then 1.5 ml (3.8 moles) of triton B at 40% in water were added all at once. After stirring for 15 hours, the medium was diluted with 90 ml of a saturated aqueous solution of sodium bicarbonate, then extracted twice with 100 ml and 50 ml of ether. The combined organic phases were washed twice with 30 ml of a saturated aqueous solution of sodium bicarbonate, then filtered through a short column of sodium sulfate, after having added 5 drops of pyridine. After evaporation of the solvents, the crude product was purified by flash chromatography on silica (CH$_2$Cl$_2$ 95/AcOEt 5/pyridine 0.2) to obtain 27.7 mg (45%) of the expected 17α alcohol.

2nd method 30.4 mg (58.2 µmoles) of the sulfoxides of Stage B were solubilized at ambient temperature and under argon in 4 ml of pyridine and then 0.5 ml (1.26 mmole) of triton B at 40% in water were added all at once. After stirring for 15 hours, the medium was diluted with 30 ml of a saturated aqueous solution of sodium bicarbonate and extracted with 100 ml, then 50 ml of ether. The combined organic phases were washed twice with 20 ml of a saturated aqueous solution of sodium bicarbonate, then filtered through a short column of sodium sulfate, after having added 5 drops of pyridine. After evaporation of the solvents, the crude product was purified by flash chromatography on silica (CH$_2$Cl$_2$ 95/AcOEt 5/pyridine 0.2) to obtain 13.6 mg (56%) of the expected 17α alcohol.

STAGE D: Δ4-pregnene-17α,21-diol-3,11,20-trione 0.44 ml (0.44 mmole) of 1N hydrochloric acid saturated with sodium chloride was added to 23.4 mg (56.5 µmoles) of the product of Stage C dissolved in 8.75 ml of CH$_2$Cl$_2$ at ambient temperature and under argon. The medium was vigorously stirred for 4 hours 15 minutes and then treated as previously. The crude product was purified by chromatography on silica (CH$_2$Cl$_2$ 80/Me$_2$CO 20) to obtain 11.0 mg (54%) of cortisone 1.

NMR $^1$H 300 MHz (CDCl$_3$): 6.13 (ws, 1H exch., OH); 5.73 (ws, 1H, H$_4$); 4.71 (d, 1H, H$_{21}$, $^2$J=20 Hz); 4.29 (d, 1H, H$_{21}$, $^2$J=20 Hz); 2.97 (d, 1H, H$_{12}$, $^2$J=12.5 Hz); 2.16 (d, 1H, H$_{12}$, $^2$J=12.5 Hz); 1.41 (s, 3H, Me$_{19}$); 0.65 (s, 3H, Me$_{18}$).

MS (EI): m/z=360 (M$^+$); 342 (M$^+$-H$_2$O); 301, 258, 161, 121, 105, 91 (100%).

IR (CHCl$_3$): 3490 (OH); 1705 (C=O in position 11 and 20); 1656 (C=O in position 3); 1613 (C=C). UV (EtOH): 237 (15500).

EXAMPLE 4

Δ4-pregnene-17α,21-diol-3,11,20-trione

STAGE A: 3-methoxy-17β-[20,21-(dimethylmethylenedioxy)]-Δ3,5,20-pregnatrien-17α-ol-11-one 3.10 ml (4.96 mmoles) of 1.6M n-butyllithium in hexane were added over 5 minutes to 590 µl (4.98 mmoles) of vinylene acetonide dissolved in 5 ml of tetrahydrofuran at −78° C. and under argon. After 15 minutes, the flask was placed in an acetone bath at −40° C. for 1 hour and the mixture was cooled to −78° C. 654 mg (2.08 mmoles) of 3-methoxy-Δ3,5-androstadiene-11,17-dione dissolved in 4 ml of tetrahydrofuran were added over 10 minutes. After 45 minutes, the medium was hydrolyzed at −78° C. with 50 ml of a saturated aqueous solution of sodium bicarbonate, then extracted three times with 100 ml of ether. The combined organic phases were washed with 30 ml of a saturated aqueous solution of sodium bicarbonate, then filtered through a short column of sodium sulfate after having added 5 drops of pyridine. After evaporation of the solvents, the crude product was purified by flash chromatography on silica (toluene 87/AcOEt 13/pyridine 0.2) to obtain a solution of pure 3-methoxy-20,21-[(1-methylethylidene)-bis (oxy)]-Δ3,5,20-pregnatrien-17α-ol-11-one to which 830 µl (10.4 mmoles) of N-methylimidazole was added. The evaporation of the solvents produced an oil which was used rapidly in the following sulfenylation stage.

The preceding oil and 1.46 ml (10.5 mmoles) of triethylamine were solubilized in 22 ml of anhydrous tetrahydrofuran and 5 ml of anhydrous dichloromethane at −40° C. and under argon and 300 µl (2.56 moles) of benzene sulfenyl chloride were added over 2 hours 20 minutes. The mixture was hydrolyzed at −40° C. with 50 ml of a saturated aqueous solution of sodium bicarbonate, then extracted three times with 100 ml of ether. The combined organic phases were washed three times with 30 ml of a saturated aqueous solution of sodium bicarbonate, 50 ml of a saturated aqueous solution of sodium chloride and then filtered through a short column of sodium sulfate after having added 0.5 ml of pyridine. The crude product obtained by evaporation of the solvents was stirred for 90 minutes at ambient temperature and under argon with 4.35 ml (11.02 mmoles, 40% in water) of triton B in 30 ml of dimethylsulfoxide. The medium was cooled in an ice bath and diluted with 100 ml of a saturated aqueous solution of sodium bicarbonate. The aqueous phase was extracted four times with 100 ml of ether and the combined organic phases were washed four times with 30 ml of a saturated aqueous solution of sodium bicarbonate, 50 ml of a saturated aqueous solution of sodium chloride and then filtered through a short column of sodium sulfate after having added 5 drops of pyridine. After evaporation of the solvents, the crude product was purified by flash chromatography on silica ($CH_2Cl_2$ 95/AcOEt 5/pyridine 0.2) to obtain 369 mg of the expected product.

NMR $^1$H 300 MHz ($CDCl_3$) 6.09 (s, 1H, $H_{21}$); 5.21 (m, 1H, $H_6$); 5.10 (s, 1H, $H_4$); 3.57 (s, 1H, OMe); 2.74 (wd, 1H, $H_{12alpha}$, $^2J$=12.5 Hz); 2.37 (d, 1H, $H_{12beta}$, $^2J$=12.5 Hz); 1.53 (s, 3H, C($CH_3$)); 1.50 (s, 3H, C($CH_3$)); 1.17 (s, 3H, $Me_{19}$); 0.72 (s, 3H, $Me_{18}$).

MS (SIMS NBA matrix): m/z=415 ($MH^+$); 414 ($M^+$, 100%); 397 ($MH^+$-$H_2O$); 356 ($M^+$-$Me_2CO$); 397 (397-$Me_2CO$); 154, 136.

IR ($CHCl_3$): 3588 (OH); 1703 (C=O in position 11); 1655 and 1628 (C=C); 1387 and 1374 (C($CH_3$)$_2$).

UV (EtOH): 220 (4500); 236 (21400).

STAGE B: Δ4 -pregnene-17α,21-diol-3,11,20-trione

Using the procedure of Stage D of Example 3, the expected product was obtained.

EXAMPLE 5

Δ4-pregnene-17α,21-diol-3,20-dione

STAGE A: 3-methoxy-20,21-[(1-methylethylidene)-bis (oxy)]-Δ3,5,20-pregnatrien-17α-ol 1.40 ml (2.1 mmoles) of 1.5M n-butyllithium in hexane were added over 5 minutes to 250 µl (2.09 mmoles) of vinylene acetonide dissolved in 2 ml of anhydrous tetrahydrofuran at −78° C. and under argon. After 10 minutes, the temperature of the reaction medium was left to rise to about −40° C. and the mixture was maintained for 1 hour at this temperature. 265.4 mg (0.88 mmole) of 3-methoxy-Δ3,5-androstadien-17-one dissolved in 2 ml of tetrahydrofuran were added over 5 minutes and the mixture was stirred for 30 minutes, then hydrolyzed at −40° C. with 20 ml of a saturated aqueous solution of sodium bicarbonate. The aqueous phase was extracted with 20 ml, then 80 ml of ether. The combined organic phases were washed with 20 ml of a saturated aqueous solution of sodium bicarbonate, then filtered through a short column of sodium sulfate after having added 5 drops of pyridine. After evaporation of the solvents, the crude product was purified by flash chromatography on silica (toluene 94/AcOEt 6/pyridine 0.2). The solutions of the pure expected product originating from the flash chromatography were stabilized with 23.1 mg of 4-dimethylamino-pyridine before evaporation of the solvents to obtain 353.3 mg of a white crystallized solid kept at −20° C., corresponding to 93% of pure product.

NMR $^1$H 200 MHz ($CDCl_3$+0.4% of pyridine-$d_5$) Stabilized 4-dimethylamino pyridine 6.01 (s, 1H, $H_{21}$); 5.22 (m, 1H, $H_6$); 5.12 (ws, 1H, $H_4$); 3.56 (s, 3H, OMe); 1.55 (s, 3H, C(Me)); 1.50 (s, 3H, C(Me)); 0.96 (s, 3H, $Me_{19}$); 0.91 (s, 3H, $Me_{18}$).

STAGE B: 3-methoxy-20,21-[(1-methylethylidene)-bis (oxy)]-21-(phenylsulfinyl)-Δ3,5,17(20)-pregnatriene 224.1 mg (0.56 mmole) of the alcohol of Stage A and 223 µl (2.80 mmoles) of N-methylimidazole were solubilized at −40° C. in 6 ml of anhydrous tetrahydrofuran and under argon and 390 µl (2.80 mmoles) of triethylamine were added all at once. 80 µl (0.68 mmoles) of benzene sulfenyl chloride were added over 3 hours and the mixture was hydrolyzed with 20 ml of a saturated aqueous solution of sodium bicarbonate. The aqueous phase was extracted three times with 50 ml of ether. The combined organic phases were washed twice with 20 ml of a saturated aqueous solution of sodium bicarbonate, then filtered through a short column of sodium sulfate after having added 5 drops of pyridine. After evaporation of the solvents, the crude product was purified by flash chromatography on silica (toluene 90/AcOEt 10/pyridine 0.2) to obtain the expected sulfoxides (4-diastereoisomers) which were used directly in the following epimerization stage.

E sulfoxides: 2 diastereoisomers (21R, sulfur epimers) NMR $^1$H 200 MHz (pyridine-$d_5$): 5.71 and 5.54 ppm (s, $H_{21alpha}$); 5.11 (m, 2H, $H_4$ and $H_6$); 3.31 (s, 3H, OMe).

Z sulfoxides: 2 diastereoisomers (21S, sulfur epimers) NMR $^1$H 200 MHz (pyridine-$d_5$): 5.37 and 5.31 ppm (s, $H_{21alpha}$); 5.12 (m, 2H, $H_4$ and $H_6$); 3.30 (s, 3H, OMe); 1.55 (s, 3H, $Me_{19}$); 1.16 (s, 3H, $Me_{18}$); 0.80 (s, 3H, C(Me)); 0.78 (s, 3H, C(Me)).

STAGE C: 3-methoxy-20,21-[(1-methylethylidene)bis(oxy) ]-Δ3,5,20-pregnatrien-17α-ol The sulfoxides were dissolved at ambient temperature and under argon in 2 ml of dimethylsulfoxide and 0.5 ml (1.1m mole) of triton B at 40% in methanol were added all at once. After 1 hour of stirring, the mixture was diluted with 20 ml of a saturated aqueous solution of sodium bicarbonate and then extracted twice with 50 ml of ether. The combined organic phases are washed twice with 20 ml of a saturated aqueous solution of sodium bicarbonate, then filtered through a short column of sodium sulfate after having added 5 drops of pyridine. After evaporation of the solvents, the crude product was purified by flash chromatography on silica (cyclohexane 60/iPr$_2$O 40/pyridine 0.2) to obtain the expected 17α alcohol.

NMR $^1$H 200 MHz ($CDCl_3$+0.4% pyridine-$d_5$): 6.06 (s, 1H, $H_{21}$); 5.22 (m, 1H, $H_6$); 5.13 (ws, 1H, $H_4$); 3.56 (s, 3H, OMe); 1.52 (s, 3H, C(Me); 1.51 (s, 3H, C(Me)); 0.97 (s, 3H, Me$_{19}$); 0.74 (s, 3H, Me$_{18}$).

STAGE D: Δ4-pregnene-17α,21-diol-3,20-dione

Using the procedure of Example 3, Stage D, the expected product was obtained.

Various modifications of the process of the invention may be made without departing from the spirit or scope thereof and it should be understood that the invention is intended to be limited only as defined in the appended claims.

What we claim is:

1. A process for the preparation of a compound of the formula

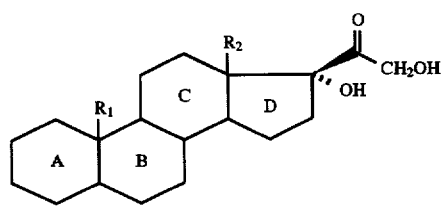

wherein R$_1$ is hydrogen or alkyl of 1 to 4 carbon atoms, R$_2$ is alkyl of 1 to 4 carbon atoms and the A, B, C and D ring system has at least one double bond and the A, B, C and D rings are optionally substituted by at least one member of the group consisting of optionally protected hydroxy, optionally protected keto, halogen, alkyl and alkoxy of 1 to 4 carbon atoms, and alkenyl and alkynyl of 2 to 4 carbon atoms comprising reacting a compound of the formula

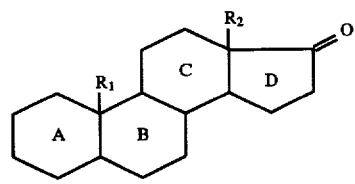

wherein R$_1$, R$_2$, A, B, C and D are as defined above with a reagent of the formula

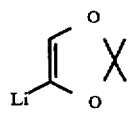

to obtain a compound of the formula

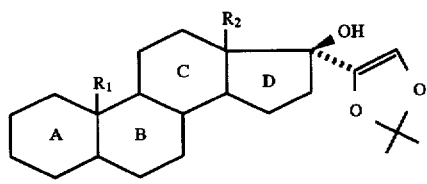

wherein R$_1$, R$_2$, A, B, C and D are as defined above, reacting the compound of formula III with an aryl sulfenyl halide of the formula

Ar-S-Hal wherein Ar is an optionally substituted phenyl and Hal is halogen in the presence of a base to obtain intermediately a compound of the formula

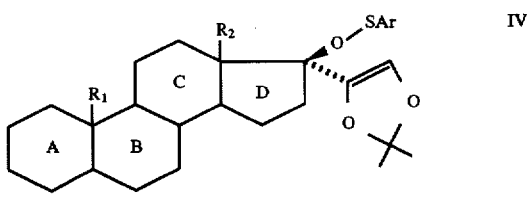

wherein Ar is defined as above which is rearranged by allowing the temperature to rise to ambient temperature optionally in the presence of a base into the sulfoxide of the formula

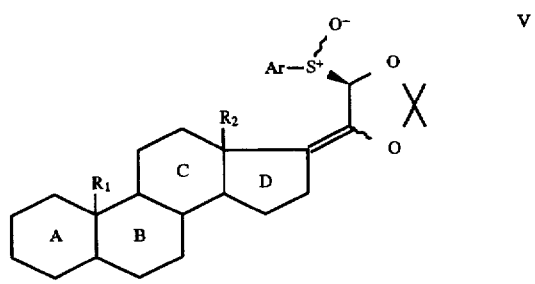

which is in the form of a mixture of diasteroisomers of E+Z configuration at the level of the 17(20) double bond, epimerizing the mixture of compounds of formula V with a strong base in an aqueous or alcoholic polar medium to obtain the sulfoxides of the formula

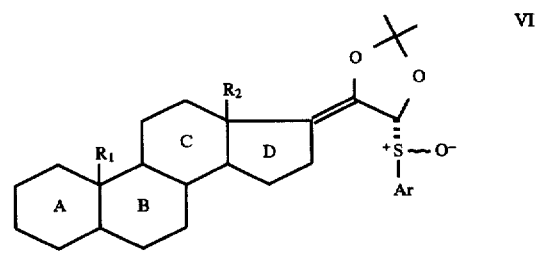

which are in form of a mixture of diastereoisomers of (Z) configuration at the level of the 17(20) double bond and which are in equilibrium with the sulfenate of the formula

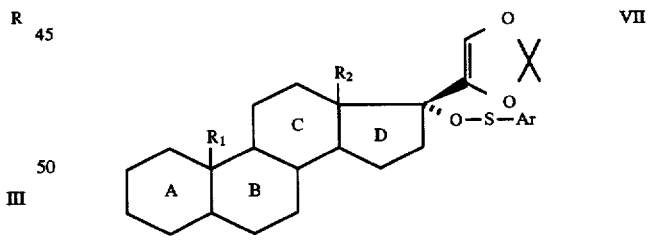

cleaving the compound of formula VII with a thiophilic compound to obtain a compound of the formula

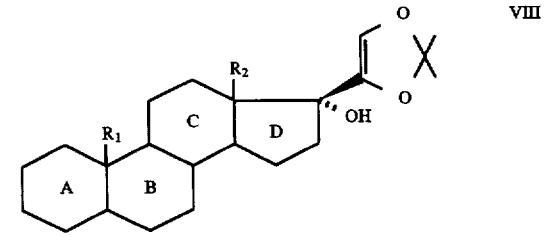

and reacting the compound of formula VIII with an acid hydrolysis agent to obtain the compound of formula I.

2. The process of claim 1 wherein the compound of formula II has the formula

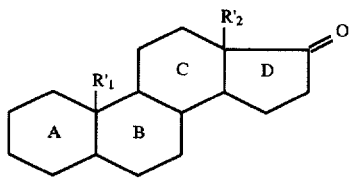

wherein $R'_1$ is hydrogen or methyl, $R'_2$ is methyl or ethyl and nuclei A, B, C and D carry at least one of the double bond configurations selected 1(2); 3(4); 9(11); 3(4) and 5(6); 4(5) and 6(7); 1(2) and 4(5); 1,3,5(10); and 1(2), 4(5) and 6(7) and are optionally substituted by at least one member of the group consisting of hydroxyls in position 3, 9 and/or 11, by one or two ketone functions in position 3 and/or 11, wherein the ketone function in position 3 is protected, by one or two fluorine, chlorine or bromine in position 6 and/or 9α, by one or more methyl or ethyl in position 2, 6, 7 and/or 16α or 16β, by one or two methoxy or ethoxy in position 3 and/or 11β, by a vinyl or allyl in position 6 or 11β or by an ethynyl in position 6 or 11β.

3. The process of claim 1 wherein the compound of formula II has the formula

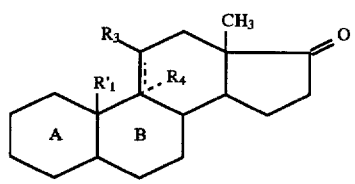

wherein $R'_1$ is hydrogen or methyl, the dotted line in position 9(11) is an optional second bond, $R_3$ is selected from the group consisting of hydrogen, oxo or hydroxy optionally protected in the form of an ether or ester, $R_4$ is selected from the group consisting of hydrogen, hydroxy and fluorine, rings A and B are one of the following

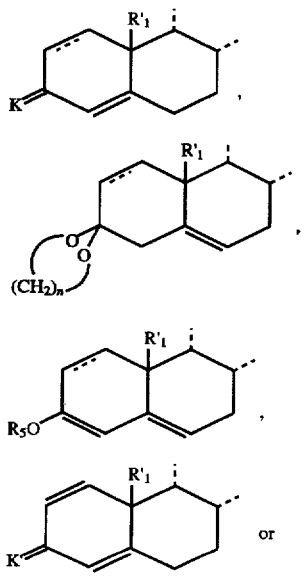

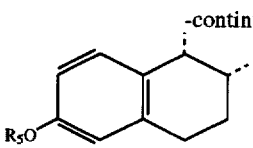

in which the dotted line in ring A is an optional second bond, K is oxo protected in the form:

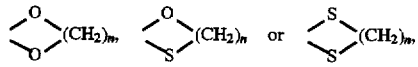

n being equal to 2 or 3, $R_5$ is an ether or ester remainder, K' is oxo protected in the form of an oxime, hydrazone or semi-carbazone.

4. The process of claim 1 wherein the sulfenylation agent of formula S is selected from the group consisting of phenyl, ortho-nitrophenyl and 3,4-dinitrophenyl sulfenyl chloride or bromide.

5. The process of claim 1 wherein the sulfenylation reaction is carried out in the presence of a base which is a tertiary amine selected from the group consisting of triethylamine, pyridine, 4-dimethylamino-pyridine, N-methylimidazole, diazabicyclo-octane and a mixture of tertiary amines.

6. The process of claim 5 wherein an excess of base is added to the reaction medium.

7. The process of claim 6 wherein the strong base used to epimerize the mixture of compounds of formula V is selected from the group consisting of hydroxides of ammonium, alkali metal hydroxides and alkali metal carbonates or bicarbonates.

8. The process of claim 7 wherein the strong base is selected from the group consisting of N-benzyltrimethylammonium hydroxide, tetrabutylammonium hydroxide, sodium hydroxide, potassium hydroxide and lithium hydroxide.

9. The process of claim 7 wherein the operation is carried out in methanol and in the presence of a cosolvent of dimethylsulfoxide or dimethylformamide.

10. The process of claim 1 wherein cleavage of the sulfenate is carried out by the action of alkali metal hydroxides, ammonium hydroxides, alkali metal carbonates or bicarbonates, trialkyl phosphite, a secondary amine or a thiolate.

11. The process of claim 1 wherein the hydrolysis of the compound of formula VIII is carried out by the action of an acid, either in a homogeneous medium, or in diphasic medium, in the presence of water and a halogenated organic cosolvent or an ester or an ether or an aromatic solvent.

12. The process of claim 1 wherein the compounds of the formulae III to VII are not isolated.

* * * * *